United States Patent [19]
Bookwalter et al.

[11] Patent Number: 5,365,921
[45] Date of Patent: Nov. 22, 1994

[54] FLIP-UP STERNAL RETRACTOR

[76] Inventors: John R. Bookwalter, 9 Belmont Ave., Brattleboro, Vt. 05301; William H. Bookwalter, 337 College St., Burlington, Vt. 05401

[21] Appl. No.: 7,909

[22] Filed: Jan. 22, 1993

[51] Int. Cl.⁵ ............................... A61B 17/02
[52] U.S. Cl. ................................ 128/20; 128/17; 269/261; 403/150
[58] Field of Search .................... 128/17-20; 403/79, 78, 100, 150; 269/258, 261, 210

[56] References Cited

U.S. PATENT DOCUMENTS

| | | | |
|---|---|---|---|
| 1,456,116 | 5/1923 | Bessesen, Sr. | 128/20 |
| 2,642,862 | 6/1953 | Jackson | 128/20 |
| 2,751,902 | 6/1956 | Loeffler | 128/17 |
| 3,853,120 | 12/1974 | Batista | 128/20 |
| 3,965,890 | 6/1976 | Gauthier | 403/79 X |
| 4,151,837 | 5/1979 | Millard, Jr. et al. | 128/20 X |
| 4,238,123 | 12/1980 | Bardes | 269/258 X |
| 4,627,421 | 12/1986 | Symbas et al. | 128/20 |
| 4,850,630 | 7/1989 | Davies | 269/258 X |
| 5,088,472 | 2/1992 | Fakhrai | 128/20 |

*Primary Examiner*—Richard J. Apley
*Assistant Examiner*—Donna L. Maraglio
*Attorney, Agent, or Firm*—Donald W. Meeker

[57] ABSTRACT

Arched arms fit over the contour of the chest cavity. Retractor blades are attached to the arms at one end by pivot pins allowing complete rotation vertically of the arms relative to the blades. The blades are attached to the pivot pin by joints which are slightly rotatable in a horizontal direction. Opposite the blade end, a rack bar is rigidly secured to one arm and slides through a slot in a housing at the end of the other arm, A pinion and handle in the housing moves the rack to separate the blades at the other end and bring them together again.

6 Claims, 1 Drawing Sheet

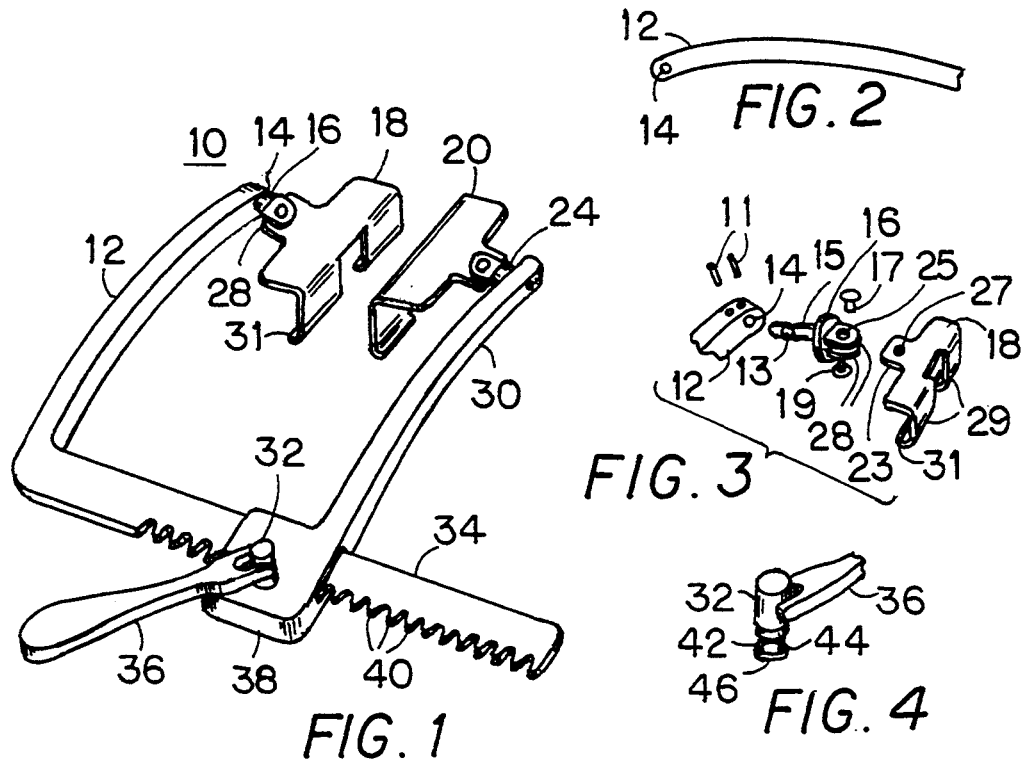
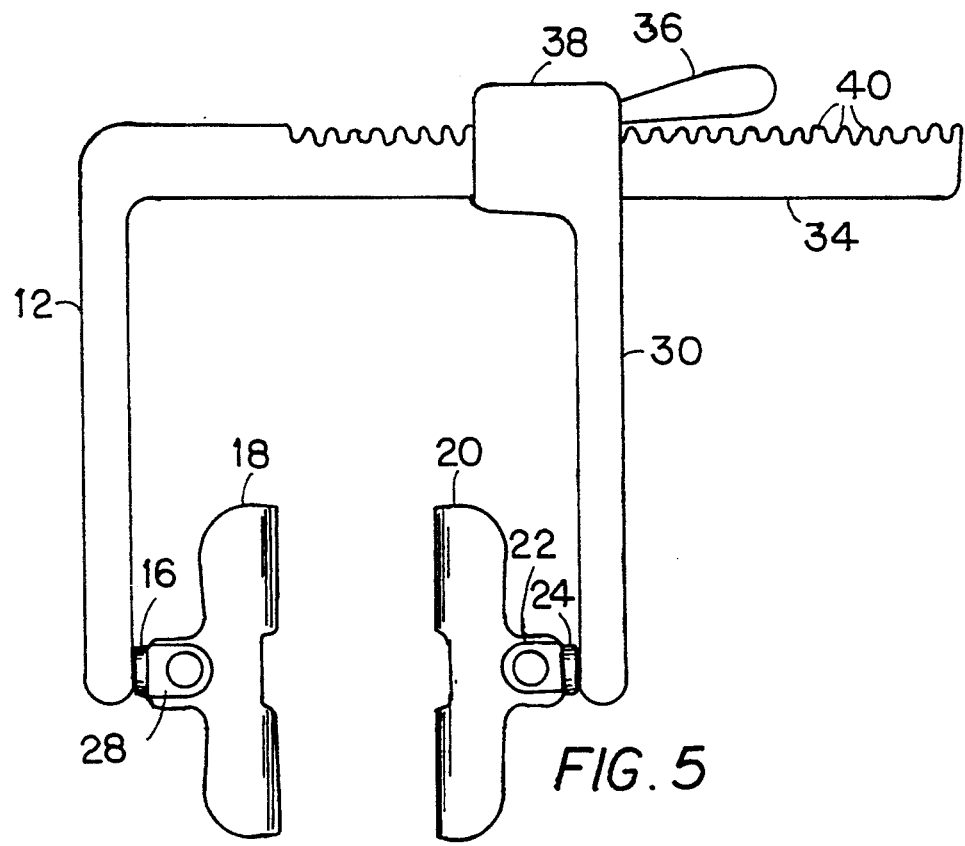

FLIP-UP STERNAL RETRACTOR

BACKGROUND OF THE INVENTION

1. Technical Field

The present invention relates to sternal retractors used in cardiac surgery and in particular to a sternal rectractor having arched arms, slightly rotatable blades, and a frame which pivots completely through a rotatable pin connection at the end of each arm between the arm and the blade.

2. Description of the Prior Art

During cardiac surgery a number of procedures are necessary requiring adequate access to the operating field around the heart. None of the prior art devices enable the sternal retractor to be pivoted so that the track mechanism may be positioned above or below the operative field.

Rigid retractor blades may put excess pressure on the shorter ribs as the sternum is separated and cause damage to the ribs and/or sternum.

Replaceable blade retractors may pose the danger of a blade being dislodged during use, or being lost when disassembled, or being misassembled.

DISCLOSURE OF INVENTION

The flip-up sternal retractor provides the cardiac surgeon with greater control of the operative field during cardiac surgery. A retractor blade is attached to each frame member at one end of the frame member by a pivot pin allowing complete rotation of the frame up away from the chest cavity of the patient, once the retractor blades have separated the sternum and are holding the chest cavity open. This allows positioning of the rack and pinion mechanism above or below the operative field. The flip-up retractor rotates up out of the way for mediastinal tube placement and is ideal for gastro-epiploic-coronary artery bypass. In the pivoted up position the invention will not place undue pressure on the trachea or carotid arteries.

Arched frame members fit over the contour of the chest cavity and thereby create a minimum profile above the chest cavity to provide less interference when the rack and pinion mechanism is positioned below the operative field.

Each blade is attached to a pivot pin by a joint which is slightly rotatable in a horizontal direction to provide flexibily in separating the sternum, thereby distributing pressure on the rib cage more evenly to prevent damage to shorter ribs and/or sternum. Broad retractor blades conform to the cut edges of the sternum to distribute the force of retraction over the broadest possible area.

A variety of different sizes of retractor blades may be installed preferably as a built-in feature at purchase to create a permanent secure fit of the retractor blade with no danger of the retractor blade slipping off.

BRIEF DESCRIPTION OF THE DRAWINGS

These and other details and advantages of our invention will be described in connection with the accompanying drawings, which are furnished only by way of illustration and not in limitation of the invention, and in which drawings:

FIG. 1 is a perspective view showing the invention with the rack in a position that would be below the operating field on a patient;

FIG. 2 is a side elevational view of an arm of the invention showing its curvature;

FIG. 3 is an exploded partial perspective view showing the pin connection of the blade to the arm;

FIG. 4 is a partial perspective view of the turning pinion mechanism;

FIG. 5 is a plan view showing the invention with the rack in a position that would be above the operating field on a patient.

BEST MODE FOR CARRYING OUT THE INVENTION

In FIG. 1 a flip-up sternal retractor 10 comprises a U-shaped frame formed by two rigid arms 12 and 30 essentially in parallel and a cross bar 34 connecting the two arms at one end. The arms are arched to correspond to a contour of a chest of a patient as seen in FIG. 2. The cross bar 34 is a rack having teeth 40 along one edge. The rack is attached to an end of one arm 12 and runs through a slot in a housing 38 attached to an end of the other arm 30. A pinion 32 turned in the housing 38 by a handle 36 serves as a mechanical means to move one arm 30 relative to the other arm 12 along the cross bar to separate the arms and bring them together. In FIG. 4 the pinion has two pins 42 and 44 attached between the pinion shaft 32 and a disc 46. The pins are separated by the distance between teeth 40 on the rack so that turning the pinion causes the rack to move.

At an end of the arms opposite the cross bar, retractor blades 18 and 20 are attached to the arms 12 and 30 by pivot pins 16 and 24 respectively for contacting and separating a sternum of a patient as the arms are separated. Each pivot pin 16 and 24 connects a retractor blade to each arm allowing 360 degree rotation of the frame relative to the blades. This enables full rotation of the cross bar 34 relative to the blades 18 and 20 on the patient to flip up the frame from a position with the cross bar 34 below an operating field, as in FIG. 1, to a position with the cross bar 34 above an operating field on a patient, as in FIG. 5.

In FIG. 3 the pivot pin 16 comprises, at one end, a cylindrical shaft 15 with a collar groove 13 inserted in a cylindrical opening 14 in a side of an end of an arm 12 and secured therein by two holding pins 11 through the arm on two sides of the collar groove, allowing the pivot pin 16 to rotate freely while it is secured in the arm. At the other end of the pivot pin 16, a slot to receive a central edge 23 of a retractor blade is formed by two flat tabs 28 protruding from the end of the pivot pin 16. The retractor blade 18 is secured in the slot by a rivet 17 and 19 fit loosely through opening 25 in the tabs 28 and opening 27 in the retractor blade, which allows slight rotation of the retractor blade horizontally within the slot. The retractor blade has two vertical elements 29 with a curved hook portion 31 at the bottom for engaging the sternum securely.

The flip-up sternal retractor is formed preferably of stainless steel or other strong and sterilizable material.

It is understood that the preceding description is given merely by way of illustration and not in limitation of the invention and that various modifications may be made thereto without departing from the spirit of the invention as claimed.

We claim:

1. A flip-up eternal retractor comprising
    a U-shaped frame formed by two long rigid arms essentially in parallel and a cross bar connecting the two arms at one end;

mechanical means to move one arm relative to the other along the cross bar to separate the arms and bring them together;

at an end of the arms opposite the cross bar positioned between the arms, a retractor blade substantially shorter than the arms attached to each of the arms at a midpoint on each of the retractor blades for contacting and retracting each side of a sternum of a patient as the arms are separated;

a pivot means connecting each retractor blade to each arm allowing 360 degree rotation of the frame relative to the blade through a horizontal axis, thereby allowing repositioning of the cross bar either above or below the operative field without obstructing the operative field while retractor blades are engaging the sternum, wherein each pivot means comprises a pivot pin between the arm and the blade, and wherein each of said arms further comprise a transverse cylindrical opening through each of said arms adjacent to an end of the arm, and wherein the pivot pin comprises, at one end, a cylindrical shaft with a collar groove inserted in the cylindrical opening, secured therein by two holding pins through the arm on two sides of the pivot pin in the collar groove enabling the pivot pin to rotate freely within the cylindrical opening; and, at the other end, a slot to receive a central edge of the blade, which blade is secured by a rivet allowing slight rotation of the blade within the slot.

2. The invention of claim 1 wherein each blade is attached to the pivot means by a joint which is slightly rotatable horizontally.

3. A flip-up sternal retractor comprising a U-shaped frame formed by two long rigid arms essentially in parallel and a cross bar connecting the two arms at one end wherein the arms are arched to correspond to a contour of a chest of a patient;

mechanical means to move one arm relative to the other along the cross bar to separate the arms and bring them together;

at an end of the arms opposite the cross bar, positioned between the arms, a retractor blade substantially shorter than the arms wherein each of the retractor blades is attached to each of the arms at a midpoint on each of the retractor blades for contact and retracting each side of a sternum of a patient as the arms are separated, wherein each retractor blade is attached to a pivot means by a joint which is slightly rotatable horizontally wherein each pivot means comprises a pivot pin connecting the retractor blade to the arm allowing 360 degree rotation of the frame relative to the blades through a horizontal axis, thereby permitting the cross bar to be positioned above or below the operative field without obstructing the operative field during a cardiac surgical procedure through a vertical midline sternal incision.

4. The invention of claim 3 wherein each of said arms further comprise a transverse cylindrical opening through each of said arms adjacent to an end of the arm, and wherein the pivot pin comprises, at one end, a cylindrical shaft with a collar groove inserted in the cylindrical opening, secured therein by two holding pins through the arm on two sides of the pivot pin in the collar groove enabling the pivot pin to rotate freely within the cylindrical opening; and, at the other end, a slot to receive a central edge of the blade, which blade is secured by a rivet allowing slight rotation of the blade within the slot.

5. A flip-up sternal retractor comprising a U-shaped frame formed by two long rigid arms essentially in parallel and a cross bar connecting the two arms at one end;

mechanical means to move one arm relative to the other along the cross bar to separate the arms and bring them together:

at an end of the arms opposite the cross bar positioned between the arms, a retractor blade substantially shorter than the arms attached to each of the arms at a midpoint on each of the retractor blades for contacting and retracting each side of a sternum of a patient as the arms are separated;

a pivot means connecting each retractor blade to each arm allowing 360 degree rotation of the frame relative to the blade through a horizontal axis, thereby allowing repositioning of the cross bar either above or below the operative field without obstructing the operative field while the retractor blades are engaging the sternum, wherein each blade is attached to the pivot means by a joint which is slightly rotatable horizontally.

6. The invention of claim 5 wherein the pivot means comprises a pivot pin between the arm and the blade.

* * * * *